US009775521B2

(12) United States Patent
Tesanovic et al.

(10) Patent No.: US 9,775,521 B2
(45) Date of Patent: \*Oct. 3, 2017

(54) REMOTE PATIENT MANAGEMENT SYSTEM

(71) Applicant: KONINKLIJKE PHILIPS N.V., Eindhoven (NL)

(72) Inventors: Aleksandra Tesanovic, Eindhoven (NL); Harald Reiter, Aachen (DE)

(73) Assignee: Koninklijke Philips N. V., Eindhoven (NL)

( * ) Notice: Subject to any disclaimer, the term of this patent is extended or adjusted under 35 U.S.C. 154(b) by 0 days.

This patent is subject to a terminal disclaimer.

(21) Appl. No.: 14/963,749

(22) Filed: Dec. 9, 2015

(65) Prior Publication Data
US 2016/0089030 A1     Mar. 31, 2016

Related U.S. Application Data

(63) Continuation of application No. 13/974,189, filed on Aug. 23, 2013, now Pat. No. 9,232,894.

(60) Provisional application No. 61/693,433, filed on Aug. 27, 2012.

(51) Int. Cl.
| | |
|---|---|
| G08B 19/00 | (2006.01) |
| G08B 21/00 | (2006.01) |
| G08B 23/00 | (2006.01) |
| A61B 5/00 | (2006.01) |
| A61B 5/0205 | (2006.01) |
| A61B 5/021 | (2006.01) |
| A61B 5/024 | (2006.01) |
| A61B 5/145 | (2006.01) |

(52) U.S. Cl.
CPC .......... *A61B 5/0022* (2013.01); *A61B 5/0205* (2013.01); *A61B 5/7275* (2013.01); *A61B 5/742* (2013.01); *A61B 5/746* (2013.01); *A61B 5/7475* (2013.01); *A61B 5/021* (2013.01); *A61B 5/024* (2013.01); *A61B 5/14532* (2013.01); *A61B 5/14546* (2013.01)

(58) Field of Classification Search
CPC .................................................. G06F 19/3418
See application file for complete search history.

(56) References Cited

U.S. PATENT DOCUMENTS

| 6,234,964 B1 | 5/2001 | Iliff | |
|---|---|---|---|
| 6,383,136 B1 | 5/2002 | Jordan | |
| 2009/0069642 A1* | 3/2009 | Gao | A61B 5/02055 600/300 |
| 2010/0268304 A1* | 10/2010 | Matos | G06F 19/3418 607/60 |

(Continued)

*Primary Examiner* — Firmin Backer
*Assistant Examiner* — Jerold Murphy

(57) ABSTRACT

A remote patient management system comprising a display and a processor. Execution of instructions cause the processor to: determine at least one first boundary value between a safe zone and a warning zone for each of at least one patient vital sign; determine at least one second boundary value between the warning zone and an alert zone for each of the at least one patient vital sign; repeatedly receive the at least one patient vital sign; determine a status value indicating the safe zone, warning zone, or alert zone; calculate a transition risk value; and display a patient status indicator which indicates the status level and the transition risk.

20 Claims, 6 Drawing Sheets

(56) References Cited

U.S. PATENT DOCUMENTS

| | | | |
|---|---|---|---|
| 2011/0046498 A1* | 2/2011 | Klap | A61B 5/0205 |
| | | | 600/534 |
| 2012/0136221 A1 | 5/2012 | Kileen et al. | |
| 2012/0200507 A1* | 8/2012 | Flam | G06F 19/322 |
| | | | 345/173 |
| 2012/0320079 A1* | 12/2012 | Feddes | G06T 11/206 |
| | | | 345/593 |
| 2013/0027411 A1* | 1/2013 | Hebler | G06F 19/3418 |
| | | | 345/501 |

\* cited by examiner

REMOTE PATIENT MANAGEMENT SYSTEM

CROSS-REFERENCE TO PRIOR APPLICATIONS

This application is a continuation of U.S. Ser. No. 13/974,189, filed on Aug. 23, 2013 which claims priority of U.S. Provisional Application Ser. No. 61/693,433, filed Aug. 27, 2012 and are incorporated by reference herein.

TECHNICAL FIELD

The invention relates to remote patient management systems, in particular to the generation of a patient status indicator which indicates a current status level of the patient and the transitional risk of the status level changing.

BACKGROUND OF THE INVENTION

Current telemonitoring systems are designed to manage adverse events and reduce the possibility that chronic patients will have health emergencies. Namely, they are able to detect when the health status of the patient is severely deteriorating to the point of re-admissions, e.g., weight significantly increased to the point of decompensation in heart failure patients. What is actually desired, and called for by the medical community, is an ability keep the patient within a safe zone for that patient, a zone in which patient is feeling optimally well for his chronic condition. In this zone the patient is maintaining his health (as opposed to look out for acute events). This is an approach to acute events prevention rather than acute events management as employed in current telemonitoring solutions. Approach like this would also allow for a progression of the disease to be modified rather than only managed, and the significant positive impact to clinical outcomes.

SUMMARY OF THE INVENTION

The invention provides for a remote patient management system, a computer program product, and a computer-implemented method in the independent claims. Embodiments are given in the dependent claims.

This invention may provide a method that can be integrated into existing or new telemonitoring systems to keep the patient in a safe, health maintenance zone. This is done by means of identifying three zones, green (safe, health maintenance zone), yellow (warning or worrying zone), and red (alert zone) and determining patients health maintenance status in relation to these zones, as well as a relation to the risk of transitioning from one zone to another. Based on this, a set of actions is computed to be suggested to the nurse or a patient that would help to keeping the patient within its green zone by modifying the progress of the disease toward the green zone.

As will be appreciated by one skilled in the art, aspects of the present invention may be embodied as an apparatus, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer executable code embodied thereon.

Any combination of one or more computer readable medium(s) may be utilized. The computer readable medium may be a computer readable signal medium or a computer readable storage medium. A 'computer-readable storage medium' as used herein encompasses any tangible storage medium which may store instructions which are executable by a processor of a computing device. The computer-readable storage medium may be referred to as a computer-readable non-transitory storage medium. The computer-readable storage medium may also be referred to as a tangible computer readable medium. In some embodiments, a computer-readable storage medium may also be able to store data which is able to be accessed by the processor of the computing device. Examples of computer-readable storage media include, but are not limited to: a floppy disk, a magnetic hard disk drive, a solid state hard disk, flash memory, a USB thumb drive, Random Access Memory (RAM), Read Only Memory (ROM), an optical disk, a magneto-optical disk, and the register file of the processor. Examples of optical disks include Compact Disks (CD) and Digital Versatile Disks (DVD), for example CD-ROM, CD-RW, CD-R, DVD-ROM, DVD-RW, or DVD-R disks. The term computer readable-storage medium also refers to various types of recording media capable of being accessed by the computer device via a network or communication link. For example a data may be retrieved over a modem, over the internet, or over a local area network. Computer executable code embodied on a computer readable medium may be transmitted using any appropriate medium, including but not limited to wireless, wireline, optical fiber cable, RF, etc., or any suitable combination of the foregoing.

A computer readable signal medium may include a propagated data signal with computer executable code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device.

'Computer memory' or 'memory' is an example of a computer-readable storage medium. Computer memory is any memory which is directly accessible to a processor. 'Computer storage' or 'storage' is a further example of a computer-readable storage medium. Computer storage is any non-volatile computer-readable storage medium. In some embodiments computer storage may also be computer memory or vice versa.

A 'processor' as used herein encompasses an electronic component which is able to execute a program or machine executable instruction or computer executable code. References to the computing device comprising "a processor" should be interpreted as possibly containing more than one processor or processing core. The processor may for instance be a multi-core processor. A processor may also refer to a collection of processors within a single computer system or distributed amongst multiple computer systems. The term computing device should also be interpreted to possibly refer to a collection or network of computing devices each comprising a processor or processors. The computer executable code may be executed by multiple processors that may be within the same computing device or which may even be distributed across multiple computing devices.

Computer executable code may comprise machine executable instructions or a program which causes a processor to perform an aspect of the present invention. Computer executable code for carrying out operations for aspects of the present invention may be written in any combination of one or more programming languages, including an object oriented programming language such as Java, Smalltalk, C++ or the like and conventional procedural programming languages, such as the "C" programming language or similar programming languages and compiled into machine executable instructions. In some instances the computer executable code may be in the form of a high level language or in a pre-compiled form and be used in conjunction with an interpreter which generates the machine executable instructions on the fly.

The computer executable code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described with reference to flowchart illustrations and/or block diagrams of methods, apparatus (systems) and computer program products according to embodiments of the invention. It will be understood that each block or a portion of the blocks of the flowchart, illustrations, and/or block diagrams, can be implemented by computer program instructions in form of computer executable code when applicable. It is further under stood that, when not mutually exclusive, combinations of blocks in different flowcharts, illustrations, and/or block diagrams may be combined. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

A 'user interface' as used herein is an interface which allows a user or operator to interact with a computer or computer system. A 'user interface' may also be referred to as a 'human interface device.' A user interface may provide information or data to the operator and/or receive information or data from the operator. A user interface may enable input from an operator to be received by the computer and may provide output to the user from the computer. In other words, the user interface may allow an operator to control or manipulate a computer and the interface may allow the computer indicate the effects of the operator's control or manipulation. The display of data or information on a display or a graphical user interface is an example of providing information to an operator. The receiving of data through a keyboard, mouse, trackball, touchpad, pointing stick, graphics tablet, joystick, gamepad, webcam, headset, gear sticks, steering wheel, pedals, wired glove, dance pad, remote control, and accelerometer are all examples of user interface components which enable the receiving of information or data from an operator.

A 'display' or 'display device' as used herein encompasses an output device or a user interface adapted for displaying images or data. A display may output visual, audio, and or tactile data. Examples of a display include, but are not limited to: a computer monitor, a television screen, a touch screen, tactile electronic display, Braille screen, Cathode ray tube (CRT), Storage tube, Bistable display, Electronic paper, Vector display, Flat panel display, Vacuum fluorescent display (VF), Light-emitting diode (LED) displays, Electroluminescent display (ELD), Plasma display panels (PDP), Liquid crystal display (LCD), Organic light-emitting diode displays (OLED), a projector, and Head-mounted display.

A content element as used herein is content which may be provided to a patient and which may be integrated into a care plan for the patient. A care plan is a day-to-day plan for managing a disease or health condition. Content elements may be provided either by a hospital or an outpatient clinic or a disease management organization or a remote patient management (RPM) system, resulting in the proprietary nature of the content elements as well as assessments. The generation of these assessments is time consuming and requires human expertise. As a result these assessments are not automatically available, leading to the unmet needs mentioned above.

In one aspect the invention provides for a remote patient management system comprising a display for displaying a graphical user interface. The remote patient management system further comprises a computing device comprising a processor. The computing device further comprises a memory containing machine-readable instructions. Execution of the instructions cause the processor to determine at least one first boundary value which defines a transition between a safe zone and a warning zone for each of the at least one patient vital sign. Execution of the instructions further cause the processor to determine at least one second boundary value which defines a transition between a warning zone and an alert zone for each of the at least one patient vital sign.

A patient vital sign as used herein encompasses a numerical value of a measurement performed by a sensor on a patient or subject. A vital sign may for instance be such things as the weight, blood pressure, pulse, SpO2, bio-impedance, or a value indicative of the internal chemistry of a patient or subject for instance the blood sugar level. Each of the patient vital signs has defined a safe zone which is defined as a region which is normal and healthy for the patient or subject.

The warning zone is a region which indicates that the health of the patient or subject may be in jeopardy and that when the vital sign is in the warning zone there may be a need for intervention or a change in the behavior of the subject. The boundary values such as the first boundary value and the second boundary value may be defined by receiving an input from an operator or healthcare provider. The determination of the boundary values may also be determined by performing data mining on existing medical records. Depending upon the patient vital sign the safe zone may be ordered by one or two warning zones. For instance if the vital sign has a particular range and if the value is unhealthy if it is above or below this safe zone then there may be two warning zones. Likewise there may be one or two alert zones which indicate that the health of the subject is in danger.

Execution of the instructions further causes the processor to repeatedly receive the at least one patient vital sign. The remote patient management system is therefore actively monitoring the patient vital signs. Execution of the instructions further cause the process to display an alert on the display if any of the at least one patient vital sign value is in the alert zone. That is to say if any of the patient vital signs is within the alert zone then an alert is displayed on the display. Other actions may also be triggered such as an alert being sent directly to a mobile telecommunications device that a doctor or healthcare provider has.

Execution of the instructions further cause the processor to set a status value to alert value if any of the at least one patient vital sign is in the alert zone. The alert value is simply a flag or other indicator. The status value may be thought of as being an internal variable or register or value used by the processor to track which of the possible values the status value has. Execution of the instructions further cause the processor to set a status value to warning value if any of the at least one patient vital sign values is in the warning zone and the alert is not displayed on the display. Execution of the instructions further cause the processor to set the status value to safe value if each of the at least one patient vital sign is within the safe zone.

Execution of the instructions further cause the processor to calculate a transition risk value using the at least one patient vital sign, the at least one first boundary value, and the at least one second boundary value. The transition risk value is descriptive of a transition of the status value to warning value if the status value is safe value the transition risk value is descriptive of a transition of the status value to alert value if the status value is warning value. Essentially the transition risk is a risk of the subject having his or her status value changed to the next higher level. The higher level is a level indicating a higher health risk. Execution of the instructions further causes the processor to display a status indicator on the display. The patient status indicator indicates the status level and the transition risk.

Execution of the instructions further causes the processor to display a set of actions on the display. The actions are selected from the database using the status value and the transition risk. This embodiment may be beneficial because it provides a means of enabling the monitoring of patient vital signs such that the health of the patient is optimally maintained. As opposed to simply waiting for a patient vital sign to deteriorate to the point where corrective action is needed the future health status of the subject is predicted and this is used to suggest actions or to control the operation of the remote patient management system to help maintain the health of the subject.

The patient vital signs could be received from an instrument, via manual input such as input typed by a subject, and/or from another system or database. For instance the system may also access health records of the insurance company and/or hospital or doctor.

In another embodiment the remote patient management system further comprises a home infrastructure device. The home infrastructure device comprises at least one diagnostic medical device for measuring the at least one patient vital sign. The at least one patient vital sign is received from the home infrastructure device.

For instance the diagnostic medical device may include, but is not limited to: a scale, a blood sugar meter, a blood pressure measurement device, a thermometer, and a blood alcohol meter.

In another embodiment execution of the instructions further cause the processor to receive a selection of the set of actions from the user interface in response to displaying the set of actions on the display. Execution of the instructions further causes the processor to generate an action message in response to the selection. Execution of the instructions causes the processor to send the action message to the home device. This embodiment may be beneficial because the combination of the patient status indicator and the set of actions form a graphical user interface for controlling the operation of the remote patient management system. The patient status indicator is easier for an operator to understand and restricted set of actions chosen using the patient status indicator are selected and displayed on the display. This may therefore reduce the cognitive burden of an operator of the remote patient management system to select actions which are appropriate to maintain the health of the subject or patient. The action message may be executed by the home infrastructure device.

In another embodiment execution of the instructions further causes the processor to select a selection of the set of actions using the status value and the transition risk. Execution of the instructions causes the processor to generate an action message in response to the selection. Execution of the instructions further causes the processor to send the action message to the home infrastructure device. In this embodiment the remote patient management system displayed the set of actions and the patient status indicator but it took its own action and automatically generated the action message. This may be beneficial when a healthcare provider is not available to review the patient status indicator or when the transition risk value is below a predetermined threshold. For instance this embodiment may be triggered when the transition risk is below a particular threshold and it is not necessary for a healthcare provider to review it.

In another embodiment the action message is operable for causing the home device to re-measure a predetermined patient vital sign. For instance the action message may specify that the patient re-measure or that the system re-automatically re-measures a particular patient vital sign. This may be useful in the case where a value is particularly out of line and causes a transition from the safe value to the warning value or the alert value. The action messages may be operable for causing the home device to display a content element on a home indicator display. A content element may for instance be a message to the subject to change his or her behavior, it may display a quiz to determine information from the subject, it may be a survey to obtain behavioral data on the subject, or it may be an educational content element to provide training to the patient which enables the patient to behave in a more healthy fashion.

In another embodiment the at least one vital sign is a single vital sign. There are two first boundary values, and there are two second boundary values. There is a first warning zone and a second warning zone. There is a first alert zone and a second alert zone. The patient status indicator comprises a safe region for indicating the safe zone. The patient status indicator has a first warning region for indicating the first warning zone. The patient status indicator has a second warning region for indicating the second warning zone. The patient status indicator has a first warning region for indicating the first warning zone. The patient status indicator has a second warning region for indicating the second warning zone. The safe region is adjacent to the first warning zone and the second warning zone. The first warning zone is adjacent to the first alert zone. The second warning zone is adjacent to the second alert zone. In some embodiments the safe region may be green, the warning region may be yellow, and the alert region may be red.

In another embodiment the at least one patient vital sign are multiple patient vital signs.

In another embodiment the patient status indicator comprises a safe region for indicating the safe zone. The patient status indicator has a warning region for indicating the warning zone. The patient status indicator has an alert region for indicating the warning zone. The status region is adjacent to the warning zone, and the warning zone is adjacent to the alert zone. In some embodiments the safe zone may be green, the warning zone may be yellow, and the alert zone may be red.

In another embodiment execution of the instructions further cause the processor to display at least a portion of the multiple patient vital signs on the display.

In another embodiment the patient status indicator is determined using a weighted average of the at least one patient vital sign.

In another embodiment the at least one zone boundary and the at least one second zone boundary are determined by any one of the following: receiving the values of the boundaries from the user interface, receiving the values from a database, determining the values using data mining techniques, determining the values using similar patient histories, and combinations thereof.

In another embodiment execution of the instructions further cause the processor to calculate a vital sign transition risk using a distance between each of the at least one patient vital signs and the first boundary value or the second boundary value. The distance or value between the vital sign and its boundary may be used as a measure of the probability that it will cross the boundary. For instance, as the value becomes closer to the boundary there is a higher probability that it will cross. A simple linear relationship can be used possibly with a weighting factor to determine the overall chance that a transition will occur.

In another embodiment the transition risk is calculated using the weighted average of the vital sign transition risk for each of the at least one patient vital sign.

In another aspect the invention provides for a computer program product comprising machine-executable instructions for execution by a processor controlling a remote patient management system. The remote patient management system comprises a display for displaying a graphical user interface. Execution of the instructions cause the processor to determine at least one first boundary value which defines the transition between a safe zone and a warning zone for each of the at least one patient vital signs. Execution of the instructions further cause the processor to determine at least one second boundary value which defines the transition between a warning zone and an alert zone for each of the at least one patient vital signs. Execution of the instructions further causes the processor to repeatedly receive the at least one patient vital sign. Execution of the instructions further cause the processor to display an alert on the display if any one of the at least one patient vital sign values is in the alert zone.

Execution of the instructions further cause the processor to set a status value to alert value if any one of the at least one patient vital sign values is in the alert zone. Execution of the instructions further cause the processor to set a status value to a warning value if any of the at least one patient vital sign value is in the warning zone and the alert is not displayed on the display. Execution of the instructions further cause the processor to set a status value to safe value if each of the at least one patient vital sign is within the safe zone.

Execution of the instructions further cause the processor to calculate a transition risk value using the at least one patient vital sign. The at least one first boundary value, and the at least one second boundary value. The transition risk value is descriptive of a transition of the status value to warning value if the status value is safe value. The transition risk value is descriptive of a transition of the status value to alert value if the status value is warning value. Execution of the instructions further causes the processor to display a patient status indicator on the display. The patient status indicator indicates the status level and the transition risk. Execution of the instructions further causes the processor to display a set of actions on the display. The actions are selected from the database using the status value and the transition risk.

In another aspect the invention provides for a computer-implemented method of controlling a remote patient management system. The remote patient management system comprises a display for displaying a graphical user interface. The method comprises the step of determining at least one first boundary value which defines a transition between a safe zone and a warning zone for each of at least one patient vital sign. The method further comprises the step of determining at least one second boundary value which defines a transition between a warning zone and alert zone for each of the at least one patient vital signs. The method further comprises the step of receiving repeatedly the at least one patient vital sign. The method further comprises the step of displaying an alert on the display if any of the at least one patient vital sign value is in alert zone.

The method further comprises the step of setting the status value to alert value if any of the at least one patient vital sign value is in the alert zone. The method further comprises the step of setting the status value to warning value if any of the at least one patient vital sign value is in the warning zone and the alert is not displayed on the display. The method further comprises the step of setting the status value to safe value if each of the at least one patient vital sign is within the safe zone. The method further comprises calculating a transitional risk value using the at least one patient vital sign. The at least one first boundary value, and the at least one second boundary value.

The transition risk value is descriptive of a transition of the status value to warning value if the status value is safe value. The transition risk value is descriptive of a transition of the status value to alert value if the status value is warning value. The method further comprises the step of displaying a patient status indicator on the display. The patient status indicator indicates the status level and the transition risk. The method further comprises the step of displaying a set of actions on the display. The actions are selected from the database using the status value and the transition risk.

It is understood that one or more of the aforementioned embodiments of the invention may be combined as long as the combined embodiments are not mutually exclusive.

BRIEF DESCRIPTION OF THE DRAWINGS

In the following preferred embodiments of the invention will be described, by way of example only, and with reference to the drawings in which.

DETAILED DESCRIPTION OF THE EMBODIMENTS

Like numbered elements in these figures are either equivalent elements or perform the same function. Elements which have been discussed previously will not necessarily be discussed in later figures if the function is equivalent.

Figure 1:
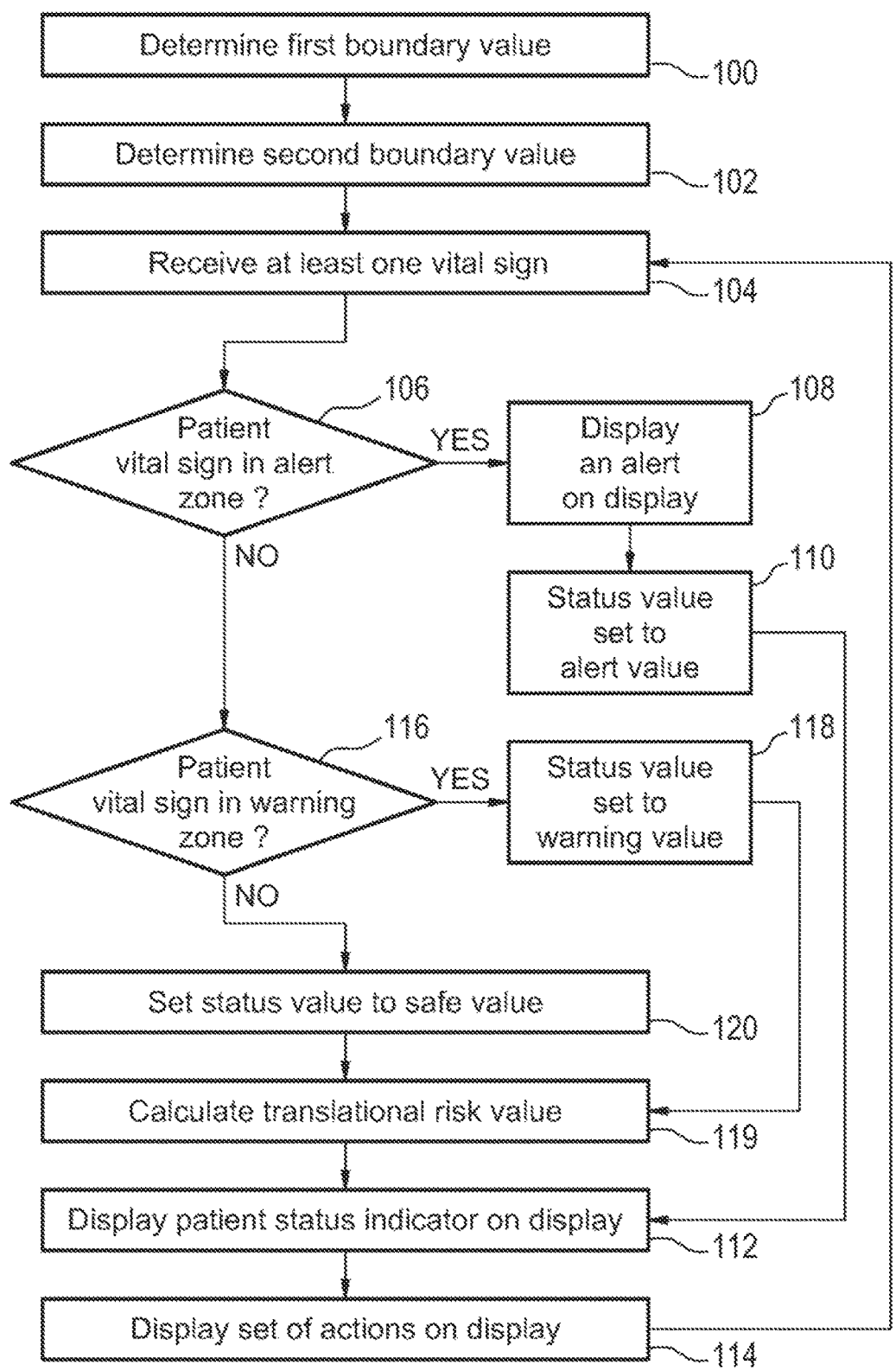
FIG. 1 shows a flow chart which illustrates a method according to an embodiment of the invention.

FIG. 1 shows a flow diagram which illustrates a method according to an embodiment of the invention. First in step 100 at least one first boundary value which defines a transition between a safe zone and a warning zone is determined for each of the at least one patient vital sign. Next in step 102 the at least one second boundary value is determined which defines a transition between the warning zone and an alert zone for each of the at least one patient vital sign. Next in step 104 at least one vital sign is received. Next block 106 is a question box and it is determined if the patient vital sign is in an alert zone. If it is yes then the method proceeds to box 108 and an alert is displayed on a display. Next in step 110 the status value is set to alert value. In step 112 the patient status indicator is then displayed on the display.

In step 114 a set of actions may be displayed on a display. Some embodiments displaying the alert on the display 108 is equivalent to the step 114. Next after step 114 the method returns back to block number 104 where at least one vital sign is received. If in block 106 at least one of the patient vital signs is not in alert zone the next question box is is at least one of the patient vital signs in a warning zone. If yes then the method proceeds from block 116 to block 118 where the status value is set to warning value. After block 118, the method proceeds to step 119 to calculate the translation risk value using the at least one first boundary value, the at least one second boundary value, and the patient vital sign. After block 119, the method then proceeds onto step 112 to display patient status indicator on the display block 114 to display a set of actions on the display and then the method returns back again to step 104 where at least one vital sign is received. In block 116 if the patient vital sign is not in a warning zone then the status value is set to safe value in block 120. After this the method proceeds to blocks 119, 112, and 114 before returning to block 104 to repeat the loop.

The loop between block 104 and 114 is repeated as long as the patient or subject is monitored by the remote patient management system.

Figure 2:
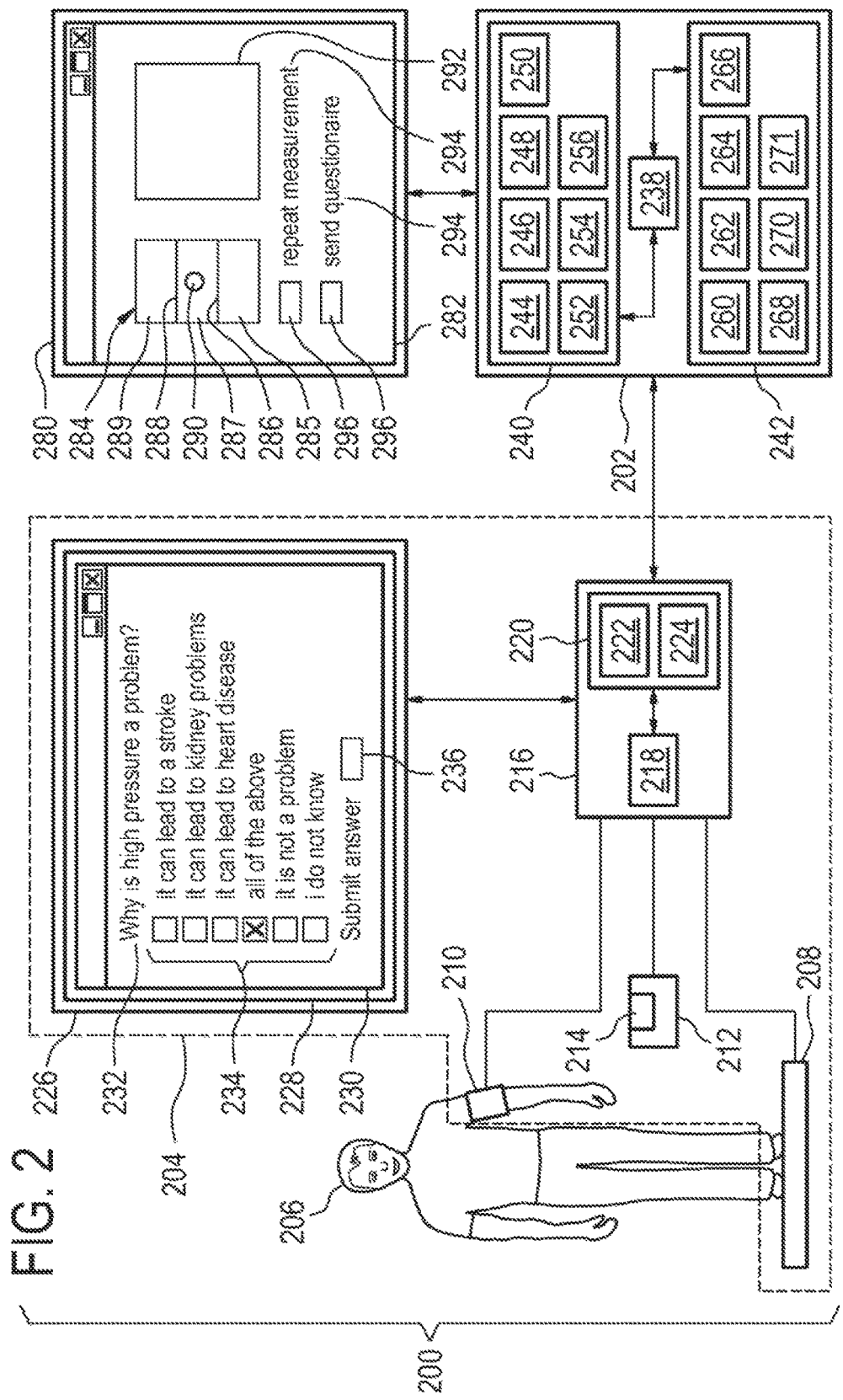
FIG. 2 illustrates a remote patient management system according to an embodiment of the invention.

FIG. 2 shows a functional diagram which illustrates a remote patient management system 200 according to an embodiment of the invention. The remote patient management system comprises a computing device 202. The computing device 202 is connected to a health professional interface 202. The computing device 200 is shown as being connected to a home infrastructure device 204 and a display 280. The home infrastructure device 204 may comprise one or more vital sign measurement devices 208, 210, 212 for measuring vital signs of the patient 206.

In this embodiment the home infrastructure device 204 comprises a scale 208 measuring the weight of the patient 206, a blood pressure cuff 210 for measuring the blood pressure of the patient 206 and a blood sugar measurement device 212 for measuring the blood sugar of a blood sample 214 from the patient 206. All three of these diagnostic medical devices 208, 210, 212 are shown as being connected to an application hosting device 216. The application hosting device 216 comprises a processor 218 which is connected to a computer memory 220. The computer memory 220 is shown as comprising a care plan 222. The care plan 222 is an executable care plan which may be executed by the processor 218 and is used for managing a chronic health condition of the patient 206.

The memory 220 of the application hosting device is operable for receiving an action message from the computing device 202. The action message causes the processor 218 to execute a predetermined response command 224. For example the response command 224 may cause the processor 218 to display the graphical user interface 228 or to modify the care plan 222.

The application hosting device 216 is shown as being connected to a feedback device 226. A feedback device is a device which allows the patient 206 to interact with the application hosting device 216. The feedback device 226 may be integrated into the application hosting device 216 or they may be separate devices which are connected or networked. In this embodiment the feedback device 226 comprises a display 228. On the display 228 is shown a graphical user interface 230. Within the graphical user interface 230 a question 232 is displayed which is a part of the assessment content element 224. Below the question 232 is a set of possible answers with check boxes that allow the patient to select an answer to the question 232. Shown below the questions and check boxes 234 is a button 236 which allows the patient 206 to submit his or her response to the question 232.

The computing device 202 comprises a processor 238. The processor 238 is connected to computer storage 240 and computer memory 242. Computer memory 242 and Computer storage 240 are both examples of computer-readable storage medium. Computer memory 242 is any memory which is directly accessible to a processor.

The computer storage 240 is shown as containing the first boundary value 244 and a second boundary value 246. The computer storage 240 is further shown as containing patient vital signs 248 received from the application hosting device 216. The computer storage 240 is further shown as containing a status value 250. The computer storage 240 is further shown as containing a transition risk value 252. The computer storage 240 is further shown as containing a database 254. The computer storage 240 is further shown as containing a set of actions 256.

The computer memory 242 is shown as containing a control module 260. The control module contains computer-executable code which enables the processor 238 to control the operation and function of the remote patient management system 200. The computer storage 242 is further shown as containing a boundary value determination module 262. The boundary value determination module 262 contains computer-executable code which enables the processor 238 to determine the first boundary values 244 and the second boundary values 246. This for instance could be from withdrawing data from the database 254 or obtaining them from a graphical user interface. The computer memory 242 is further shown as containing a status value determination module 264. The status value determination module 264 contains computer-executable code which enables the processor 238 to determine the status value 250 using the patient vital signs 248 and the first and second boundary values 244, 246. The computer memory 242 is further shown as containing a transition risk calculation module 266. The transition risk calculation module 266 contains computer-executable code which enables the processor 238 to calculate the transition risk value 252 using the first boundary value 244, the second boundary value 246 and the patient vital signs 248. The computer memory 242 is further shown as containing a database query module 268. The database query module 268 contains computer-executable code which enables the processor 238 to determine the set of actions 256 using the database 254, the transition risk value 252 and the status value 250. The computer memory 242 is further shown as containing the graphical user interface control module 270. The graphical user interface control module 270 enables the processor 238 to display a graphical user interface 282 on a display 280. The computer memory 242 is shown as containing an optional action generation module 271. The action generation module 271 is able to generate the action message either automatically or in response to a signal from the graphical user interface 282.

The display 280 is shown as being connected to the computing device 202. The display 280 is operable for displaying a graphical user interface 282. The graphical user interface has a rendering of the patient status indicator 284. The patient status indicator shows the first boundary 286 and the second boundary 288. These boundaries define the safe region 285, the warning region 287 and the alert region 289. The transition risk indicator 290 is shown in the warning region 287. Its proximity to the second boundary 288 indicates the risk of the patient changing into the alert region 289. Adjacent to the patient status indicator 284 is a region 292 where additional data such as individual patient vital signs may be displayed. Below this is a set of actions 294. Next to each individual action 294 is an action selector 296 which enables the selection of a particular action. For instance selecting an action 294 may cause the action generation module 271 to send a specific action message to the application hosting device 216.

Figure 3:
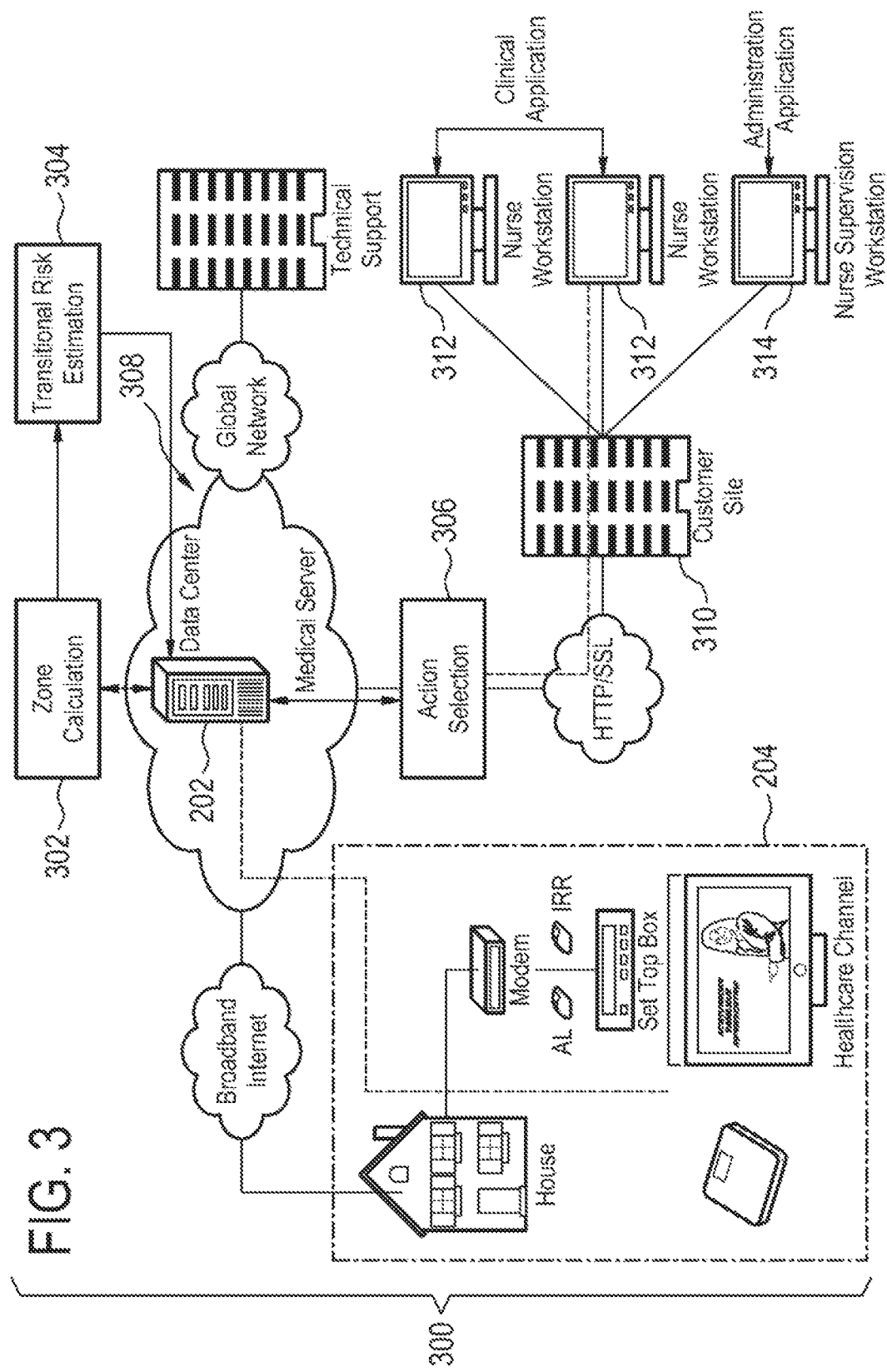
FIG. 3 illustrates a remote patient management system according to a further embodiment of the invention.

Embodiment of the invention may comprise computer executable code for performing a method which can be integrated in existing or new telemonitoring system to keep the patient in the health maintenance zone. The method may have the following modules:
1) Patient health zone calculation
2) Zone transition risk estimation
3) Action selection These modules are integrated into one system as depicted in the schematic overview in FIG. 3. FIG. 3 shows a further embodiment of a remote patient monitoring system according to an embodiment of the invention. The system also comprises a home infrastructure 204 which is connected to a host site 308. For instance this may be done using servers at a remote location possibly using cloud computing. The computing device performs zone calculation 302, transitional risk estimation 304 and may provide actions 306 to be selected. A customer site 310 such as a hospital or doctor's office may connect to the host site 308. From there individual nurse workstations 312 could be connected also with a supervisor workstation 314.

The architecture of a typical telemonitoring system 300 is presented in the schematic view. The modules of the invention utilize also communication paths of the telemonitoring systems. The sensor data or manual input of the patient (using, e.g., TV) are via a set-top box transferred to the Data centre 308. The modules for calculating zone 302 and the transitional risk 304 are making use of these data, and are also writing their results back to the common server 202. Action selection module takes the data from the server 202 for calculating the applicable actions that system suggests either to the patient 204 or to the nurse 312. These actions are then presented to either the patient or the nurse using the http/ssl connections and the internet broadband.

Figure 4:
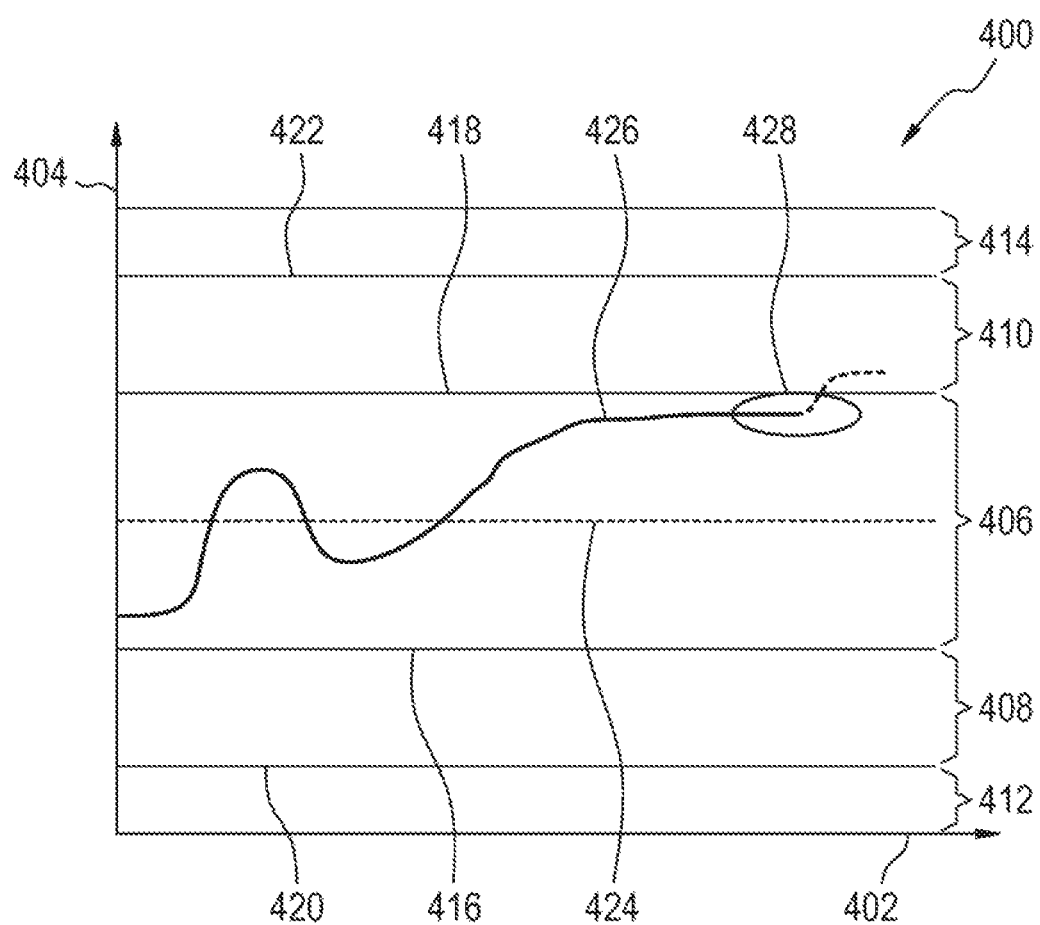
FIG. 4 illustrates a patient status indicator.

FIG. 4 shows an embodiment of a patient status indicator 400. The patient status indicator 400 is in the form of a plot which plots time 402 versus the vital sign value 404. In the middle there is a safe zone 406. Below the safe zone 406 is a first warning region 408. Above the safe zone 406 is a second warning region 410. Below the first warning region 408 is a first alert region 412. Above the second warning region 410 is a second alert region 414. The first boundary 416 separates regions 406 and 408. The first boundary 408 separates regions 406 and 410. The second boundary 420 separates regions 408 and 412. The second boundary 422 separates regions 410 and 414. The dashed line 424 indicates the optimal value of the vital sign. The vital sign is a function of time; time is plotted by the curve 426. The circle 428 indicates that the vital sign is close to the boundary 418 and that a transitional risk exists. The dashed portion of 426 shows a possible path that the vital sign may take crossing the boundary 418.

The actions are intended to keep the patient as much as possible within the safe zone 406. The safe zone 406 as depicted in FIG. 4 may be colored green in some embodiments. This is the zone where patient health status is maintained and where his signs and symptoms are in such a state that he is not in a danger of an acute event and feels optimally well for his chronic condition. The warning zone 408, 410 in the figure represents the zone in which there is a potential danger that the patient's condition might deteriorate and requires explicit actions to be taken by the patient or a nurse to modify the progression of the disease, e.g., weight increased 0.5 kg above the health maintenance zone could indicate slight worsening which, with appropriate diet and an extra pill of diuretic pills could be corrected and patient put back to the safe, green zone.

When the patient goes into the alert zone 412, 414, there is an immediate danger of an acute event and the system action should always include notifying the nurse who needs to take further actions in direct discussion with a patient. The zone boundaries can either be specified by the clinician per patient, and are, in that case, based on his clinical data and expertise. Alternatively the zones can be derived by the system using the on-line data analysis techniques on the hospital's patient population and using the similar cases find an optimal health maintenance zone per patient.

Figure 5:
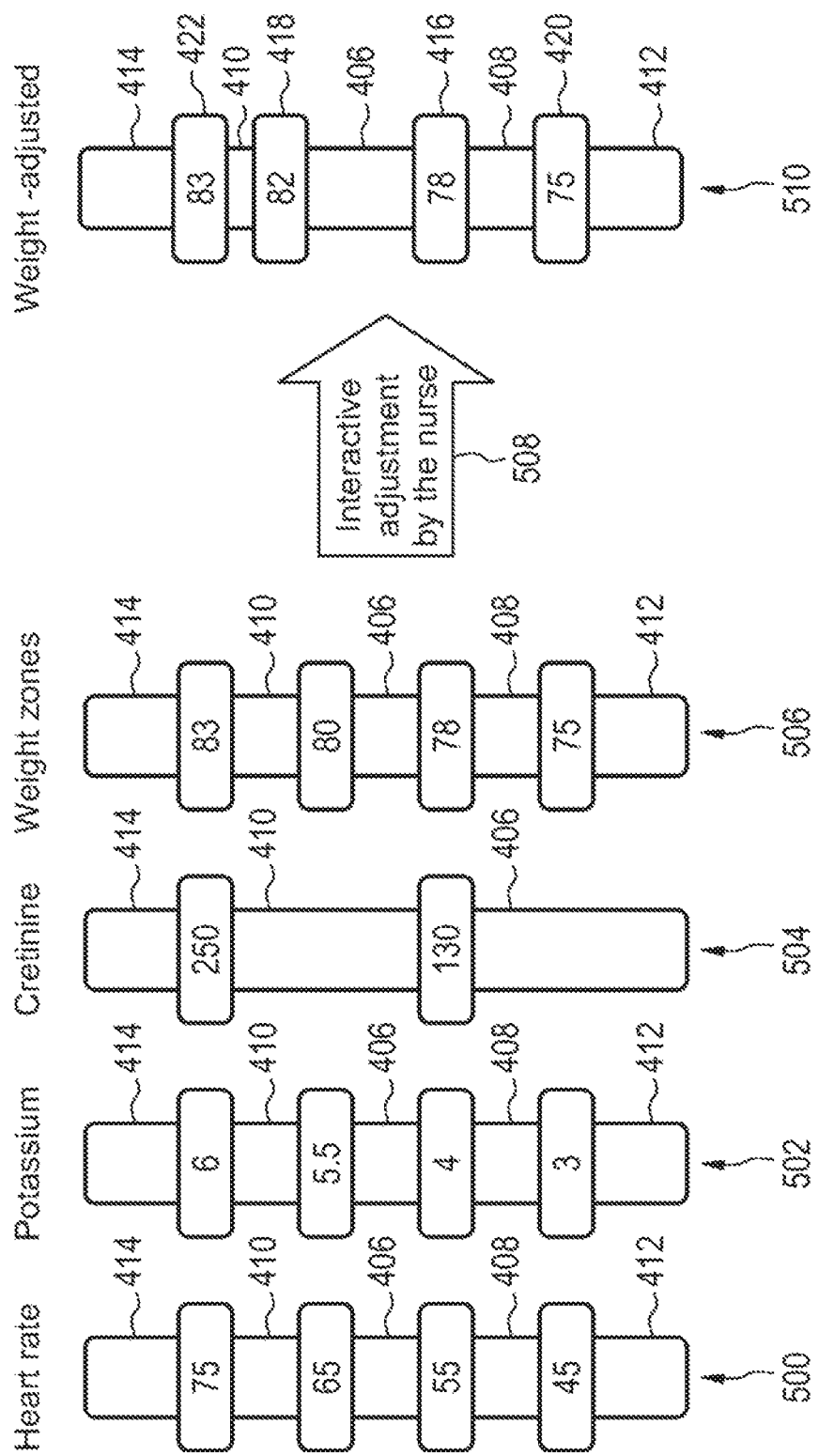
FIG. 5 illustrates how to calculate a patient zone or status value.

FIG. 5 is an illustration of how to calculate a patient zone or status value. FIG. 5 shows one way of calculating weight adjusted boundary values 422, 418, 416, 420. Individual boundary values are shown for the heart rate 500, potassium 502, 406 creatine, and weight zones 506. These may be adjusted interactively by an operator or a nurse 508 to arrive at the weight adjusted values 510.

The following paragraphs provide a more detailed description of some of the elements that may be combined (note that we assume that patient data comes from the sensors at home and that the system has an access to the electronic health record as well for additional data elements):

First patient zone calculation is discussed.

This component contains an algorithm for calculation of the zone in which the patient is. The calculation can be based on one parameter or can be multi-parametric. The calculation takes into an account the parameters that define the patient health status (e.g., weight, blood pressure, lab values, etc) and the desired thresholds of the parameters (e.g., weight should be between 78 and 85 kg as a healthy range, and everything above 87 is a problem). As mentioned, the threshold of the parameters can be derived by analyzing patient populations of the hospitals, or by means of manual input by the clinician. Each of the parameters individually can be in any of the zones (green (safe), yellow (warning), red (alert)) and their linear weighted combination is used to calculate (as shown in the FIG. 5) the overall health maintenance status of the patient. The weight of the parameters in the overall health maintenance status is proportional to the extent to which the parameter is distant to the ideal, green range.

| Measured parameter | Red | Yellow | Green zone | Yellow | Lower red |
|---|---|---|---|---|---|
| Potassium | >6 | 6-5.5 | 4-5.5 [mmol/L] | 4-3 | <3 |
| Cretinine | >250 | 250-130 | 0-130 [umol/L] | | |
| Weight | >80 | 80-83 | 78-80 [kg] | 78-75 | <75 |
| Heart rate | >75 | 75-65 | 55-65 [bpm] | 45-55 | <45 |

For example, using data mining techniques on the overall patient population database, the system could suggest the thresholds for the zones per measured parameter as shown in the table above, and visualised in the figure below. This would be presented on the graphical user interface of the nurses with the gauge that allows her to fine-tune the zones for the patient, based on her experience, as illustrated in FIG. 5.

Figure 6:
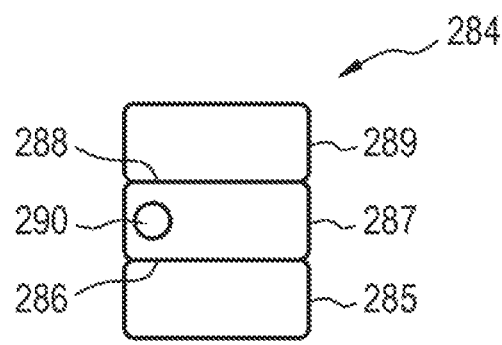
FIG. 6 shows an illustration of the patient status indicator from FIG. 2 in greater detail.

FIG. 6 shows an illustration of the patient status indicator 284 from FIG. 2 in greater detail. This basically means that nurse and clinicians will be presented with simple indication of the health status rather than the need to digest all the parameters and all the values, thereby reducing their cognitive burden.

Next, transitional risk estimation is discussed. This component contains a model of patient risk of transition from one zone to another. The risk model is derived from the distance of the health maintenance status (line in FIG. 7) to the zone border. The closeness is a percentage of the space need to cross the zone line. If the patient health maintenance status is on 50% of a zone that means it is on the middle of the green, health maintenance zone and there is no risk for transition, hence transition risk is 0%. If the health maintenance status is on 10% closeness that means that the line is on the 10th of the space of the health zone and is close to the yellow zone. Similar holds for transition from warning to alert and warning to safe. When the patient zone is already in alert, then no transitional risk needs to be calculated as the state is so serious that the nurses have been involved to provide guidance to the patient.

Figure 7:
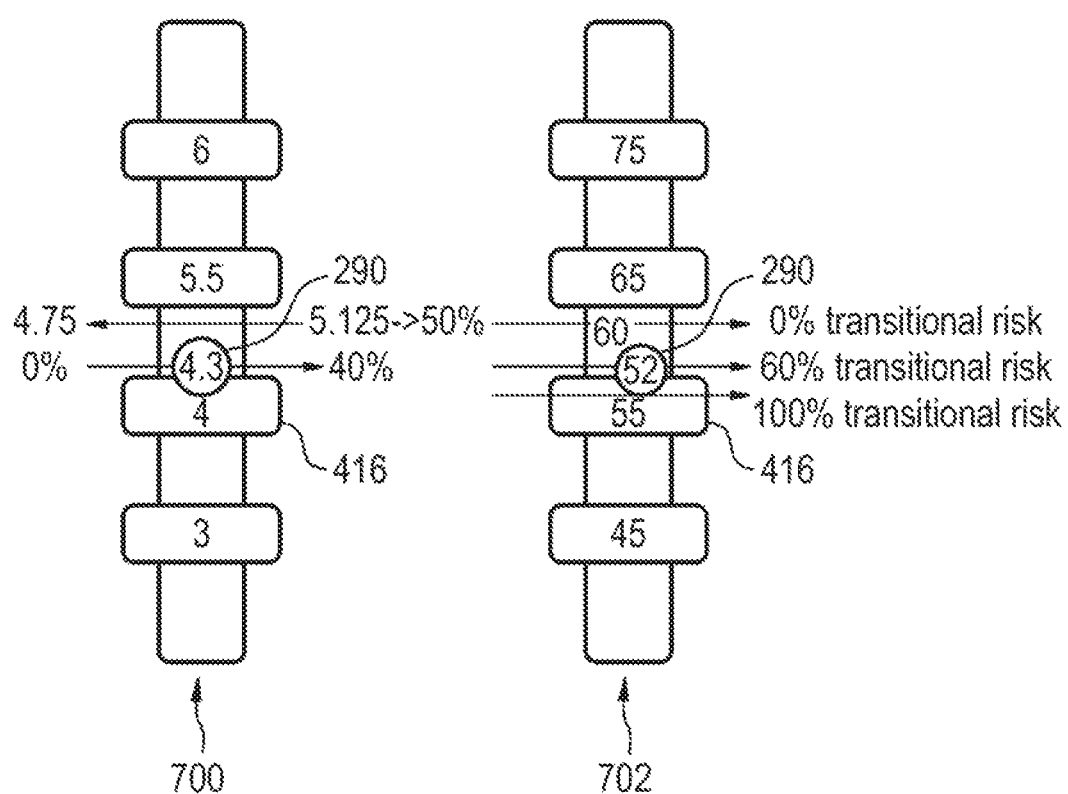
FIG. 7 illustrates the calculation of transitional risk for the combination of potassium and the heart rate.

FIG. 7 illustrates the calculation of the transitional risk for the value of the potassium 700 and the heart rate 702. In both instances the distance of the current value of the vital sign 290 is evaluated in comparison to the distance to the first boundary 416.

For example, assume that the patient's health maintenance is calculated, as is shown in FIG. 7, based on two parameters (can be any number of parameters) such as potassium (lab value) and heart rate (vital sign), both acquired from devices at patient home. Assume that the zone values for individual parameters are calculated as described in zone calculations. For potassium, that would mean that a value of 4.75 mmol/L (which is middle of the health maintenance range) represents 0% risk, while for heart rate that would be 60 bpm. This also means that 100% or risk of transition would be on 5.5 mmol/L and 4 mmol/L for potassium and 65 bpm and 55 bpm for heart rate. If patient current measurements are 4.3 mmol/L for potassium and 52 bpm for heart rate, then the value of potassium is around 40% of the transition risk while heart rate is 60%. Total transition risk in health maintenance zone is an average of these two risks, and is 50%. This would lead to no action required on the nurses behalf, and would be represented in the patient heath maintenance status as shown in FIG. 6.

Next action selection is discussed. This module takes into account the zone the patient is in, the transitional risk and decides on an action to be taken. This action can be taken directly from the database or the medical algorithms. The actions that correspond to certain patient characteristics or health maintenance status can be additionally recorded and used as means of rules to assign the actions to the similar patients in the future. An example of the actions based on the health maintenance status and risk of transition from one zone to another are shown in the table below:

| Health Maintenance status/zone | Transitional risk | Example Action |
|---|---|---|
| 50% of green | 0% | No action required |
| 30% of green | 40% transitional risk | Action include reminders to the patient to read his educational material, regularly take medications, or look a bit closer after this fluid restrictions |
| 50% yellow | 0% | Actions include specific advices for medications, e.g., taking extra pill of diuretics, and scheduling the lab follow-ups for the nurse to keep an overview of the patients' condition and is able to modify the progression of the disease |
| 20% yellow | 10% transitional risk | Advice to the nurse to consider up-titrating to the next dose of heart failure medications, and change some of the other medications patient is currently in |

While the invention has been illustrated and described in detail in the drawings and foregoing description, such illustration and description are to be considered illustrative or exemplary and not restrictive; the invention is not limited to the disclosed embodiments.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measured cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

LIST OF REFERENCE NUMERALS 200 remote patient management system
202 computing device
204 home infrastructure device
206 patient
208 scale
210 blood pressure cuff
212 blood sugar measurement device
214 blood sample
216 application hosting device
218 processor
220 memory
222 care plan
224 response command
226 feedback device
228 display
230 graphical user interface
232 assessment question
234 possible answers with checkboxes
236 submit answer button
238 processor
240 storage
242 memory
244 first boundary values
246 second boundary values
248 patient vital signs
250 status value
252 transition risk value
254 database
256 set of actions
260 control module
262 boundary value determination module
264 status value determination module
266 transition risk calculation module
268 database query module
270 graphical user interface control module
271 action message generation module
280 display
282 graphical user interface
284 patient status indicator
285 safe region
286 first boundary
287 warning region
288 second boundary
289 alert region
290 transition risk indicator
292 additional data
294 action
296 action selector
300 remote patient monitoring system
302 zone calculation
304 transitional risk estimation
306 action selection
308 host site
310 customer site
312 nurse workstation
314 supervisor workstation
400 patient status indicator
402 time
404 vital sign value
406 safe zone
408 first warning region
410 second warning region
412 first alert region
414 second alert region
416 first boundary
418 first boundary
420 second boundary
422 second boundary
424 optimal value
426 value of vital sign
428 indication of transitional risk
500 heart rate
502 potassium
504 creatine
506 weight zones
508 manual adjustment
510 weight adjusted values
700 potassium
702 heart rate

The invention claimed is:

1. A remote patient management system comprising:
a display for displaying a graphical user interface;
a plurality of sensors configured to measure vital signs of a patient, the sensors including a scale configured to measure a weight of the patient, a blood pressure cuff configured to measure a blood pressure of the patient, and a blood sugar sensor configured to measure blood sugar of a blood of the patient; and
a computing device comprising a processor, wherein the computing device further comprises a memory containing machine readable instructions, wherein execution of the instructions cause the processor to:
retrieve from the memory at least one first boundary value which defines a transition between a safe zone and a warning zone for individual ones of the vital signs of the patient;
retrieve from the memory at least one second boundary value which defines a transition between the warning zone and an alert zone for individual ones of the vital signs of the patient;
receive values of the vital signs of the patient as measured by the sensors;
set a status value to alert if one or more of the values of the vital signs of the patient is in the alert zone;
set the status value to warning if one or more of the values of the vital signs of the patient is in the warning zone and the alert is not displayed on the display;
set the status value to safe if one or more of the values of the vital signs of the patient is within the safe zone; and
calculate a vital sign transition risk using a distance between individual ones of the vital signs of the patient and the first boundary value or the second boundary value.

2. The remote patient management system of claim 1, wherein the processor calculates the transition risk value using the values of the vital signs of the patient, the at least one first boundary value, and the at least one second boundary value, wherein the transition risk value is descriptive of a transition of the status value to warning if the status value is safe, wherein the transition risk value is descriptive of a transition of the status value to alert if the status value is warning.

3. The remote patient management system of claim 2, wherein the display displays a patient status indicator, wherein the patient status indicator indicates the status level and the transition risk.

4. The remote patient management system of claim 3, wherein the display displays a set of actions, wherein the actions are selected from a database using the status value and the transition risk.

5. The remote patient management system of claim 4, wherein the remote patient management system further comprises a home infrastructure device, wherein the home infrastructure device comprises at least one diagnostic medical device for measuring the vital signs of the patient; wherein the values of the vital signs of the patient is received from the home infrastructure device.

6. The remote patient management system of claim 5, wherein execution of the instructions causes the processor to receive a selection of the set of actions from the user interface in response to displaying the set of actions on the display, wherein execution of the instructions causes the processor to generate an action message in response to the selection, wherein execution of the instructions causes the processor to send the action message to the home infrastructure device.

7. The remote patient management system of claim 6, wherein the action message is operable for causing the home device to re-measure a predetermined patient vital sign and display a content element on a home indicator display.

8. The remote patient management system of claim 5, wherein execution of the instructions causes the processor to select a selection of the set of actions using the status value and the transition risk, wherein execution of the instructions causes the processor to generate an action message in response to the selection, wherein execution of the instructions causes the processor to send the action message to the home infrastructure device.

9. The remote patient management system of claim 8, wherein the action message is operable for causing the home device to re-measure a predetermined patient vital sign and display a content element on a home indicator display.

10. The remote patient management system of claim 1, wherein the vital signs of the patient include a single vital sign, wherein there are two first boundary values, wherein there are two second boundary values, wherein there is a first warning zone and a second warning zone, wherein there is a first alert zone and a second alert zone, wherein the patient status indicator comprises a safe region for indicating the safe zone, wherein the patient status indicator has a first warning region for indicating the first warning zone, wherein the patient status indicator has a second warning region for indicating the second warning zone, wherein the patient status indicator has a first warning region for indicating the first warning zone, wherein the patient status indicator has a second warning region for indicating the second warning zone, wherein the safe region is adjacent to the first warning zone and the second warning zone, wherein the first warning zone is adjacent to the first alert zone, and wherein the second warning zone is adjacent to the second alert zone, and
wherein the processor calculates the vital sign transition risk using a distance between the single vital sign and any of the boundary values.

11. The remote patient management system claim 1, wherein the vital signs of the patient include multiple patient vital signs.

12. The remote patient management system of claim 11, wherein the patient status indicator comprises a safe region for indicating the safe zone, wherein the patient status indicator has a warning region for indicating the warning zone, wherein the patient status indicator has an alert region for indicating the warning zone, wherein the safe region is adjacent to the warning zone, and wherein the warning zone is adjacent to the alert zone.

13. The remote patient management system of claim 11, wherein execution of the instructions further causes the processor to display at least a portion of the vital signs of the patient on the display.

14. The remote patient management system of claim 1, wherein the patient status indicator is determined using a weighted average of the vital signs of the patient.

15. The remote patient management system of claim 1, wherein the at least one first boundary value and the at least one second boundary value are:
received from the user interface;
retrieved from a database;
determined using data mining techniques;
and/or determined using similar patient histories.

16. The remote patient management system of claim 1, wherein the processor is further configured by the machine readable instructions to
effectuate presentation of a question to the patient;
effectuate presentation of a set of possible answers corresponding to the question; and
receive an answer submitted by the patient.

17. The remote patient management system of claim 1, wherein the transition risk is calculated using a weighted average of the vital sign transition risk for individual ones of the vital signs of the patient.

18. A computer-implemented method of controlling a remote patient management system, wherein the remote patient management system comprises a display for displaying a graphical user interface, a plurality of sensors configured to measure vital signs of a patient, the sensors including a scale configured to measure a weight of the patient, a blood pressure cuff configured to measure a blood pressure of the patient, and a blood sugar sensor configured to measure blood sugar of a blood of the patient, and a computing device including a processor configured by machine readable instructions, wherein the method comprises the steps of:
receiving, by the processor, at least one first boundary value which defines a transition between a safe zone and a warning zone for individual ones of the vital signs of the patient,
receiving, by the processor, at least one second boundary value which defines a transition between a warning zone and an alert zone for individual ones of the vital signs of the patient;
receiving, by the processor, values of the vital signs of the patient as measured by the sensors;
setting, by the processor, a status value to alert if any of the values of the vital signs of the patient is in the alert zone;
setting, by the processor, the status value to warning if any of the values of the vital signs of the patient is in the warning zone and the alert is not displayed on the display;
setting, by the processor, the status value to safe if individual ones of the values of the vital signs of the patient are within the safe zone, wherein the at least one first boundary value and the at least one second boundary value are:
received from the user interface;
retrieved from a database;
determined using data mining techniques;
and/or determined using similar patient histories; and
calculating a vital sign transition risk using a distance between individual ones of the vital signs of the patient and the first boundary value or the second boundary value.

19. The computer-implemented method of claim 18, wherein the method further comprises:
calculating the transition risk value using the values of the vital signs of the patient, the at least one first boundary value, and the at least one second boundary value, wherein the transition risk value is descriptive of a transition of the status value to warning if the status value is safe, wherein the transition risk value is descriptive of a transition of the status value to alert if the status value is warning.

20. The computer-implemented method of claim 18 further comprising:
effectuating, by the processor, presentation of a question to the patient;
effectuating, by the processor, presentation of a set of possible answers corresponding to the question; and
receiving, by the processor, an answer submitted by the patient.

* * * * *